(12) United States Patent
Shepard et al.

(10) Patent No.: US 6,235,369 B1
(45) Date of Patent: *May 22, 2001

(54) STRIP-FORM FASTENING AND DISPENSING

(75) Inventors: William H. Shepard, Amherst; Paul R. Erickson, New Boston, both of NH (US)

(73) Assignee: Velcro Industries B.V. (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/133,991

(22) Filed: Aug. 14, 1998

Related U.S. Application Data

(63) Continuation-in-part of application No. 08/922,292, filed on Sep. 3, 1997.
(51) Int. Cl.[7] ........................................ B32B 3/06
(52) U.S. Cl. ................ 428/85; 24/306; 221/22; 221/25; 221/70; 221/176; 221/185; 225/6; 225/15; 225/32; 225/93; 242/590; 428/40.1; 428/41.8; 428/42.1; 428/43; 428/99; 428/100; 428/906
(58) Field of Search ................ 428/40.1, 41.8, 428/42.1, 99, 100, 906, 85, 43; 221/22, 25, 70, 176, 185; 225/15, 32, 6, 93; 242/590; 24/306

(56) References Cited

U.S. PATENT DOCUMENTS

| | | | |
|---|---|---|---|
| 3,197,830 | 8/1965 | Hoadley | 24/306 |
| 3,973,610 | 8/1976 | Ballin | 24/306 |
| 4,244,502 | 1/1981 | Reed | 225/13 |
| 4,267,949 | 5/1981 | Hembren | 225/106 |
| 4,340,633 * | 7/1982 | Robbins | 428/99 |

(List continued on next page.)

OTHER PUBLICATIONS

Produce bag dispenser (description included in IDS transmittal letter).

Strap product (description included in IDS transmittal letter and attached Fig. A).

*Primary Examiner*—Nasser Ahmad
(74) *Attorney, Agent, or Firm*—Fish & Richardson, P.C.

(57) ABSTRACT

A dispenser for strip materials, e.g. hook and loop fastener material, which automatically finds formations in a continuous fastener strip during its dispensing and, at that point in the dispensing procedure, produces a resistance to the remaining supply, that enables parting of the lead unit from the remaining supply, thus dispensing a discrete unit. The dispenser has a receptacle to hold the supply of fastener strip material; it employs a retarding device to provide light drag against the motion of the strip as the leading strip unit moves from the dispenser in response to pull by a user. A detent downstream of the retarding device engages a corresponding formation in the strip material to resist movement of the remaining strip material, so that the strip ruptures along a line of weakness under a user's tension. Also disclosed are dispensable fastener strips of various forms, some advantageously formed by use of needled bat, and methods of forming the fastening strips.

51 Claims, 11 Drawing Sheets

U.S. PATENT DOCUMENTS

| | | | |
|---|---|---|---|
| 4,384,664 | 5/1983 | Roos | 225/106 |
| 4,770,322 * | 9/1988 | Slota | 221/240 |
| 4,794,028 | 12/1988 | Fischer | 428/100 |
| 4,883,197 | 11/1989 | Sanchez et al. | 221/26 |
| 4,893,381 | 1/1990 | Frankel | 24/442 |
| 5,048,158 | 9/1991 | Koerner | 24/442 |
| 5,056,682 * | 10/1991 | Meyst | 221/25 |
| 5,118,022 | 6/1992 | Farahnik | 225/106 |
| 5,133,671 | 7/1992 | Boghosian | 439/371 |
| 5,168,603 | 12/1992 | Reed | 24/442 |
| 5,207,368 | 5/1993 | Wilfong, Jr. et al. | 225/106 |
| 5,294,034 | 3/1994 | Svensson | 225/106 |
| 5,433,363 | 7/1995 | Simhaee | 225/47 |
| 5,480,084 | 1/1996 | Daniels | 225/106 |
| 5,518,795 | 5/1996 | Kennedy et al. | 428/100 |
| 5,556,019 | 9/1996 | Morris | 225/96 |
| 5,573,168 | 11/1996 | Kannankeril et al. | 225/106 |
| 5,605,729 | 2/1997 | Mody et al. | 428/37 |
| 5,630,526 | 5/1997 | Moody | 221/45 |
| 5,802,676 | 9/1998 | Tolan | 24/16 R |
| 5,810,200 | 9/1998 | Trokhan | 221/55 |
| 5,813,585 | 9/1998 | Kannankeril et al. | 225/106 |
| 5,868,275 * | 2/1999 | Moody | 221/33 |
| 5,921,433 | 7/1999 | Friar et al. | 221/25 |
| 5,934,535 | 8/1999 | Kannankeril et al. | 225/106 |

* cited by examiner

COVER OPEN FOR LOADING

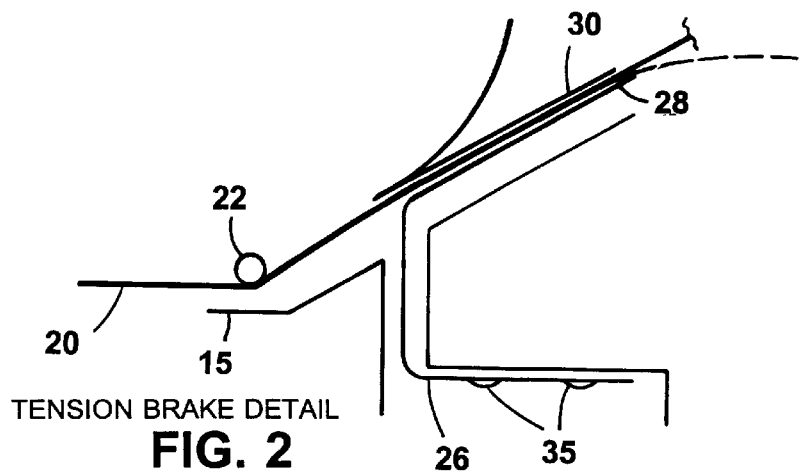
TENSION BRAKE DETAIL
FIG. 2
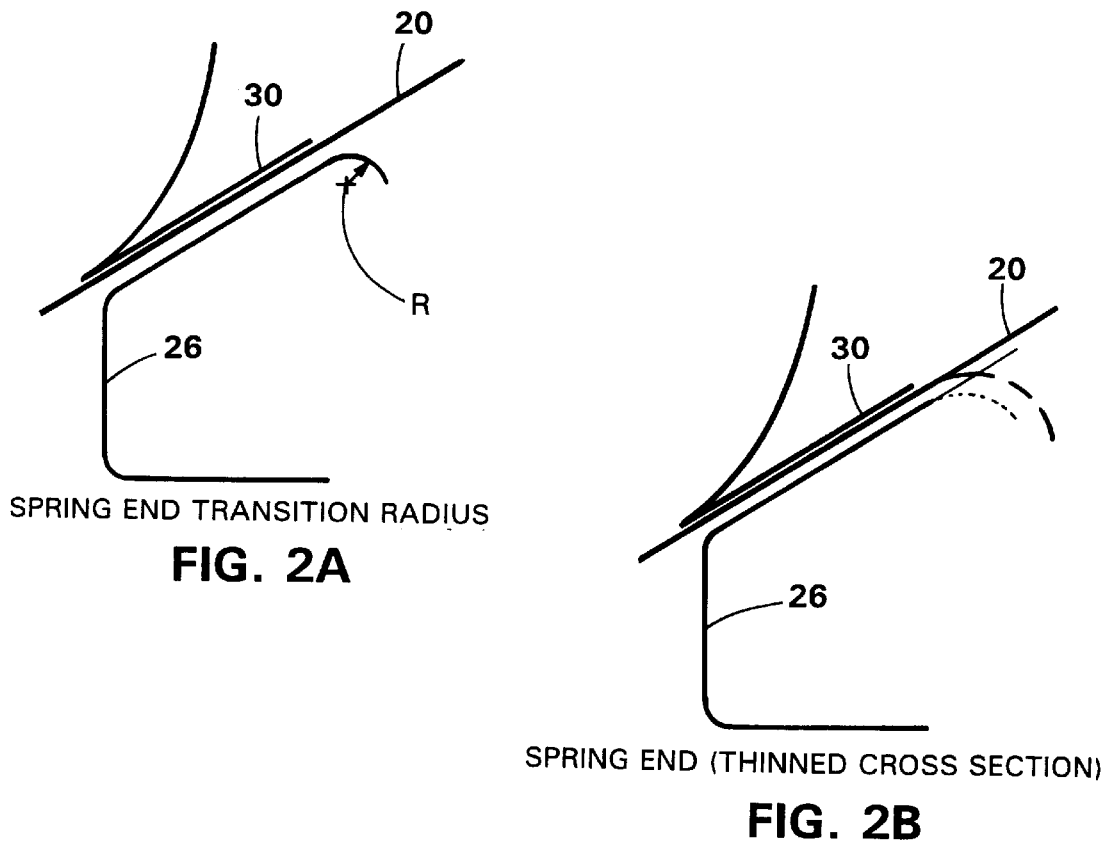
SPRING END TRANSITION RADIUS
FIG. 2A
SPRING END (THINNED CROSS SECTION)
FIG. 2B

STRAP SLIDING OVER CLAW AS
STRAP IS BEING DISPENSED

STRAP ENGAGED WITH CLAW
IMMEDIATELY BEFORE BREAKAGE

TOP VIEW:
STRAP ENGAGED WITH CLAW
IMMEDIATELY BEFORE BREAKAGE (COVER REMOVED FOR CLARITY)

STRIP-FORM FASTENING AND DISPENSING

BACKGROUND OF THE INVENTION

This application is a continuation in part of pending U.S. Ser. No. 08/922,292 filed on Sep. 3, 1997, entitled FASTENER LOOP MATERIAL, ITS MANUFACTURE, AND PRODUCTS INCORPORATING THE MATERIAL.

This invention relates to dispensing fasteners and other items made in continuous strip form and to fastener strips suitable for dispensing.

The invention in one aspect concerns an overall system including a dispenser and a cooperating continuous strip of fastener units that leads to lower cost and wider applicability of fastening by the hook and loop technique.

Elongated strips of hook and loop fasteners are used as straps or ties for bundling and wrapping products, for applying identification markings to products, etc.

Previously, a continuous strip of fastener units has been provided with cross-perforations or lines of weakness spaced at predetermined interval lengths to define the individual units, which can be detached from one another. In some cases, the strip is wound upon itself to form a supply roll. The user uncoils a unit from the roll, finds the line of weakness, and breaks it from the supply roll by tension. Time can be lost in finding the line of weakness, and if a mistake is made, two units instead of one may be detached.

Other items made in continuous sequence as a continuous strip, to be detached at lines of weakness, present similar problems.

SUMMARY OF THE INVENTION

A dispenser device is provided which automatically finds the second unit in a continuous strip during dispensing of a leading unit and, during the dispensing procedure, automatically applies resistance to the second unit, so that pull on the leading unit parts it from the remaining supply. The labor saved by automatically singulating a strip-form unit decreases cost and increases convenience, especially in the case of touch fasteners.

It is also realized that, by providing a dispenser that is convenient to use, there are potential large volume applications for strip-form fastener units for marking, bundling, or wrapping a wide variety of products that include banding or bundling of wires, fiber optic cables, hydraulic or pneumatic tubes, and many other products that are typically grouped together for use or for sale.

In a preferred form, a supply of strip-form fastener units is provided as a roll. Dispensing is achieved by the user grasping the free end of the roll and pulling it across a mechanism which finds the second unit, locks on to it and applies strong resistance to its movement, so that, as the user continues to pull, the leading unit breaks away from the next unit under tensile force. In a preferred form, the device which senses the strip and resists movement of the next-succeeding unit automatically releases the remaining unit when the perforation is broken. In preferred forms, the next succeeding strip-form unit, which now becomes the leading unit, is automatically lifted and presented to be grasped for repeating the procedure.

In preferred forms, the dispenser also has a mechanism which continuously applies light drag resistance to the strip material being pulled from the roll so that pull on the roll does not cause it to overrun or result in improper action.

In its preferred form, the device which senses the strip and resists movement of the next-succeeding unit automatically releases the remaining unit when the perforation is broken.

In a preferred form, a formation is provided on each unit of the strip material and a detent, in preferred form a simple claw, engages the formation applies the resistance to the second unit so that tension on the lead unit breaks it away.

Preferably the sensing and strong resisting action is performed by a detent over which the strip material slides during dispensing movement.

Advantageously, the strip-form units are provided with an inherent curling tendency or set (curl memory) from having been wound in a roll, and the supply roll is so arranged in the dispenser, that this curling characteristic serve to help raise the end of the lead strip unit, to present it to be grasped.

The techniques of the invention are applicable to many strip materials, but in particular, to fastener materials, especially hook and loop fastener components such as hook strips, loop strips, strips having hooks on one side and loops on the other, and strips having pressure sensitive adhesive or other fastening features on one or both sides.

An inexpensive fastener material, capable of being dispensed by this technique, is two-sided material, having fastener hooks on one side and loop material on the other, formed by in situ molding and laminating in which the resin that forms at least part of the base layer of the hooks serves also as the bonding agent for adhering the needled non woven loop material to the base layer.

In a particularly effective system, the strip-form fastener units comprise molded fastener hooks to which is directly bonded a needled and stretched non-woven material whose loops or fibers are constructed and arranged to be engaged by the hooks. Advantageously this product is formed by the in situ molding techniques.

Another fastener material especially adapted for the dispensing techniques disclosed is a tape having hooks or loops on one surface and pressure sensitive adhesive on the other side, the tape having special formations that enable the dispensing system to function. In some cases a release liner is employed on the adhesive. In important other cases, the adhesive is formulated to releasably engage overlying portions of the tape, so that it can be supplied rolled or folded upon itself, with no release liner. For applying drag to such a tape while being withdrawn from the dispenser, it is advantageous to apply the light drag force by action of a roller, such as a roller that is spring biased against the adhesive side of the tape, which turns with the advancing adhesive, and presses the opposite side of the strip against a braking (drag) surface.

According to one particular aspect of the invention, a dispenser is provided for a supply of continuous strip material, the material having formations that include parting lines spaced at points along the length to define successive units of predetermined length, the parting lines enabling a leading unit to part from the remaining material when the material at the respective parting line is subjected to parting tension, the dispenser comprising a receptacle to hold the supply of strip material, a retarder constructed and arranged to provide drag against the motion of the material as a leading unit is removed from the dispenser in response to pull by a user, and a device, (in certain preferred embodiments located downstream of the retarder) positioned to be engaged by the strip material as the leading unit is pulled from the dispenser, the device comprising at least one detent constructed to engage a corresponding formation of the second unit following the leading unit to resist movement of the following unit so that the leading unit parts from the remaining material at the respective parting line.

Preferred embodiments of this aspect of the invention have one or more of the following features.

The receptacle of the dispenser is constructed and arranged to hold a supply of fastener strip material having parting lines defining strip-form fastener units. The dispenser is combined with a supply of fastener strip material having fastener elements on at least one of its sides, preferably the fastener elements comprising hooks or fibers or loops for hook and loop fastening or fasteners constructed for self-engageable fastening; in some advantageous cases, the fastener strip material is two-sided, having hooks on one side and hook engageable fibers or loops on the other side, and in some cases, the fastener strip material has hooks or hook-engageable fibers or loops on one side and pressure-sensitive adhesive on the other side. In certain cases, a release layer lies over the pressure sensitive-adhesive and the parting line extends into the release layer.

The detent comprises at least one stationary claw over which the strip material slides as the leading unit is pulled from the dispenser until a formation of the second unit of strip material that is engageable by the claw is engaged by the claw.

The retarder includes a resilient member that bears against the strip material as the leading unit is withdrawn. Preferably, the retarder includes a leaf spring, preferably the downstream end of the leaf spring is positioned and arranged to be resiliently deflected in response to pull on the leading unit. Preferably, the downstream end of the spring is curved away from the path of the strip material.

In certain advantageous cases, the retarder, e.g. the resilient member or spring, is constructed and arranged to position the next-following unit for grasping upon breaking of the leading unit from the remaining material. In certain cases, the resilient member is constructed and arranged to raise a portion of the strip unit immediately following the leading unit breaking from the remaining material. In some embodiments, the resilient member comprises an elongated spring member such as a leaf spring exposed for face-to-face engagement with the under-surface of the strip material, positioned to raise the end of the next-following unit when the leading unit is broken away. Preferably, the downstream end of the spring member is arranged to be resiliently deflected downwardly by withdrawing tension applied to the leading strip unit, and, upon relief of the tension as a result of breaking of the leading unit from the remaining strip material, the spring is constructed and arranged to move upwardly in restoring motion to carry with it the strip material that extends beyond the spring into position to be grasped.

In a preferred form, a leaf spring member has a main portion at the retarder and a downstream end portion of the leaf spring beyond the retarder that is thinner than the thickness of the main portion of the leaf spring, the downstream end portion arranged to be resiliently deflected during removal of a leading strip and to elastically recover upon parting of the leading unit, the spring carrying with it a corresponding portion of the successive unit.

The retarder includes a spring-loaded roller.

Hooks are integrally molded on a portion of the exterior of the dispenser, enabling the dispenser to be releasably mounted on loop material secured to a support.

The dispenser is combined with advantage with certain supplies of strip material. In certain important cases, units of the material have a slit engageable by the detent, each slit ending at a stop surface that enables the detent to stop movement of the second unit. In certain other cases, units of the strip material have formations at the leading end of each discrete strip unit, or in its main body, exposing a detainable edge portion of the unit for engagement by the detent.

In a preferred embodiment, the fastener material has sufficient stiffness and roll set (curl memory) to spring from a bent configuration as it is pulled across the detent to a straighter or reversely curved shape when the leading unit is broken from the next succeeding unit so that a portion of the next unit lifts from the detent in position to be grasped by a user for dispensing.

In a preferred form, the dispenser is constructed to hold a supply of strip material in roll form. In another form, the dispenser is constructed to hold material folded upon itself in a Z-fold. In certain embodiments, the dispenser is constructed and arranged to enable withdrawing a strip unit by one hand of a user. In certain cases, the dispenser has a base suitable for resting upon a flat surface and in certain cases it is constructed and arranged to be portable or hand-held. In some cases, the dispenser has hooks integrally molded on a portion of its exterior enabling the dispenser to be releasably mounting on loop material secured to a support. In certain cases, advantageously, the dispensing section is angled relative to the surface on which its base is supported, so that the strip unit can be withdrawn at a convenient angle, e.g. at an upward angle relative to a horizontal surface on which the base of the dispenser rests.

In a preferred form, the dispenser has edge guides for engagement by edges of the material being withdrawn from the dispenser to guide the material to be engaged by the detent in the formations provided in the material.

In another aspect of the invention, the dispenser is combined with a supply of fastener strip material having substantial lateral stiffness, the dispenser including edge guides in the vicinity of the detent to guide this fastener strip to ensure the detent engages the respective formation in the strip material.

In another aspect the dispenser is combined with a supply of fastener strip material, the material carrying arrays of fastener elements on its first and second sides, the respective fastener elements being of cooperative form capable of being releasably fastened together. In some cases, advantageously, fastener elements on the first side comprise loops or fibers of form capable of being releasably engaged by fastener elements on the second side. In certain cases, the fastener elements on the second side of the material are hooks molded integrally with a base layer, the loops or fibers being bonded to the base layer of the molded hooks by the material of the base layer.

In another aspect of the invention, which involves novel combination with the dispenser described, as well as a new fastener product per se, the first side of the material comprises a non-woven web of entangled fibers of substantial tenacity having a basis weight of between about 1.8 to 2.5 ounces per square yard. In preferred embodiments, fibers or loops are defined by a non-woven web which comprises a batt of loose, staple fibers that have been entangled and form a non-woven web structure of fibers joined at entanglements, loops of some of the fibers extending from at least one side of the web; in certain cases, the batt is of needle punched form. In some cases, the non-woven structure is bonded in a stretched state in which tightened entanglements form knots. In certain cases, the knots are bonded in a stretched state by resin integral with the material that forms the fastening elements on the second side of the strip material.

According to another aspect of the invention, an extended length of fastener material is provided that forms a series of detachable strip units suitable for use with a dispenser having a detent, the fastener material having formations that include weakened parting lines at spaced intervals along its length to define the strip units and at least one formation in each strip unit, the formation constructed and arranged to be engaged by the detent to detain the respective unit while a preceding unit is detached by rupture at the parting line by tension applied to the parting line.

Advantageously, the strip material has sufficient lateral stiffness to enable it to be guided by edge guides to register the detent with the formation of each strip unit.

Preferably, the fastener material has sufficient resiliency to spring from a bent configuration as it is pulled across a detent to a straighter shape when the leading unit is broken away from the remaining material to assist the succeeding unit to lift from the detent in position to be grasped by a user for dispensing the next successive strip unit.

A preferred method for forming a composite product having a large multiplicity of hook-form fastener projections extending from the surface of its base portion comprises the following steps: providing a cooled, rotating mold roller having inwardly extending, fixed, projection-forming cavities defined in its periphery; to the exterior of the forming roller, applying molten plastic material for filling the cavities and forming a base in the manner that incorporates a hook engageable material on the side of the base directed oppositely from the side in which the projections are formed; withdrawing the fastener material from the forming roller, including withdrawing the projections from the cavities; and either in line or as a separate batch process, forming parting lines at spaced intervals extending transversely of the resulting material.

Another preferred method for forming a fastener material comprises the steps of: forming loop product by a method comprising the steps of forming a batt of loose, staple fibers; entangling the fibers to produce a non-woven fabric of fibers joined at entanglements, with loops of some of the fibers extending from at least one side of the fabric; subsequently stretching the fabric to tighten the entanglements to form knots, and combining the back side of the loop product with the backside of a layer that carries hook fasteners. In some embodiments, prior to combining the loop product with the resin layer, a binding step is performed to bind the knots to hold the fabric in its stretched condition. In some cases, the combining step is effective to bind the knots to hold the fabric in its stretched condition. In certain cases, the step of combining is performed substantially simultaneously with forming a layer that carries the hook fasteners. In a preferred embodiment, the layer that carries the fastener hooks is formed by the method of forming a running length of fastener material having integrally formed with its base a large multiplicity of hook-forming fastener projections extending from the surface of the base portion, the method comprising: providing a cooled, rotating mold roller having inwardly extending, fixed, projection-forming cavities defined in its periphery; to the exterior of the forming roller, applying molten plastic material for filling the cavities and forming a base in the manner that incorporates the hook engageable material on the side of the base directed oppositely from the side in which the projections are formed, and withdrawing the fastener material from the forming roller, including withdrawing the projections from the cavities.

BRIEF DESCRIPTION OF THE DRAWINGS

FIG. 2 is a diagram of a tensioning system of the dispenser of FIG. 1;

FIG. 2A is a diagram of the tensioning system illustrated in FIG. 2, with an alternatively shaped spring end;

FIG. 2B is a diagram of the tensioning system illustrated in FIG. 2, having a spring with a thinned cross section;

FIG. 6 is a view similar to FIG. 1 of another dispenser construction, with an angled dispenser section, while

FIG. 11 is a longitudinal cross-sectional view of a means for manufacturing an integrally molded engaging member with backing material attached, while

DESCRIPTION OF THE PREFERRED EMBODIMENTS

Figure 1:
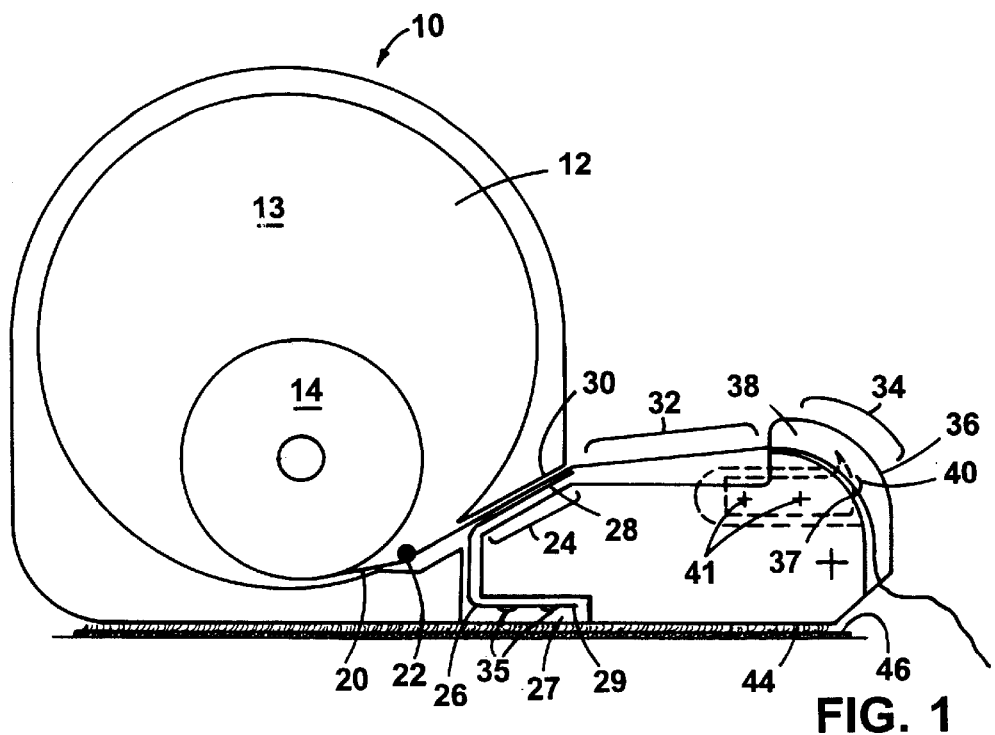
FIG. 1 is a side view of a dispenser holding a roll of fastener strap material, its cover removed.

Referring to FIGS. 1–6, dispenser 10 has a housing structure that defines supply receptacle 12, which is shaped to loosely hold roll 14 of fastener strap (or other strip form member), to permit rotation of the roll 14.

The receptacle 12 has a back wall 13, and is open at its front to enable loading by axial insertion motion of the roll 14. In FIG. 1B, tape cover 16 of the dispenser, shown in open position, is pivotally mounted to rotate about axis Y to closed position where it locks in place. After the roll 14 is loaded into the dispenser below, cover 16 pivots closed about axis Y, to confine the roll 14.

In one example, receptacle 12 and cover 16 are configured to receive a roll 14 of up to 7.5 inches diameter while in other embodiments the dispenser may be larger or smaller based on user needs. The number of straps in the roll 14 is of course determined by the roll diameter, the wind tension, and the length and thickness of the individual straps. In one embodiment, the dispenser holds a roll of 75 straps, each 18" long by 0.5" wide, the straps having thickness of about 0.040 inches, forming a roll of about 7.0 inches diameter. The wind tension is sufficient to produce a firm roll which does not easily collapse and cause jamming at the separation pin 22.

Figure 10:
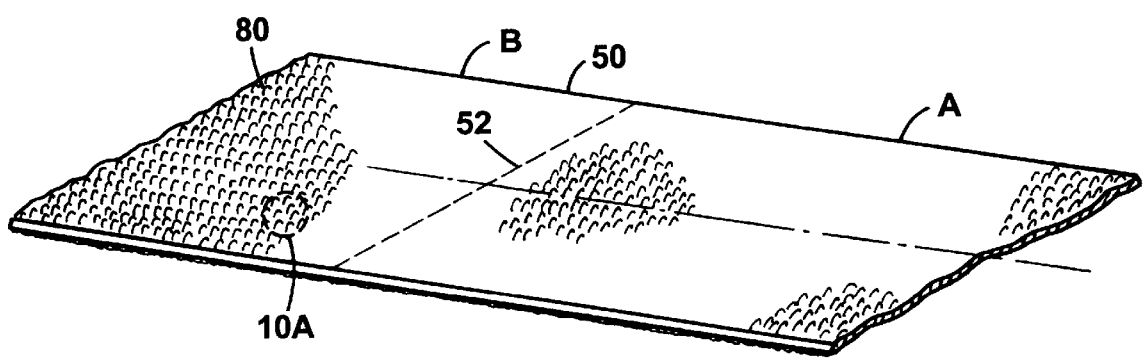
FIG. 10 is a longitudinal cross section view of a length of strap material having fastener hooks on one side and loops on the other side.
Figure 10A:
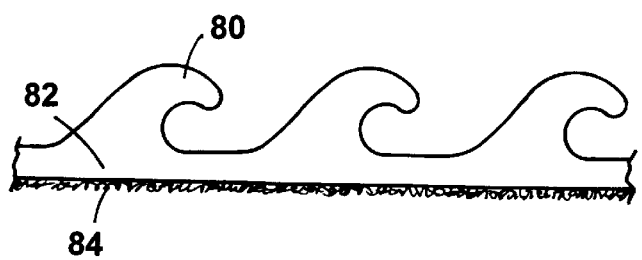
FIG. 10A is a magnified view of the material of FIG. 10.

The strap material in certain cases is a fastener hook tape or fastener loop tape, each adapted for hook and loop fastening. In the presently preferred embodiment, it is a combination tape having fastener hooks on one side and loops on the other as shown in FIGS. 10 and 10A. As will be described further below, in many applications the hook comprises a plastic strip having an array of fastener hooks molded integrally with the base layer and the loop component is a light-weight, needled, and stretched product that is in situ bonded to the base of the hook strip by the adhesive properties of the synthetic resin layer that forms the corresponding side of the base layer. The present embodiment of FIGS. 1–6 is constructed to dispense such two-sided fastener tape.

As shown in FIG. 1 and in detail in FIG. 2, in passing from the supply roll 14 along a removal path, the strap 20 being removed first passes over separation pin 22. Pin 22 extends parallel to axis Z of the supply roll 14, and is located at a height even with support surface 15. The effect of the strap passing under the separation pin, combined with the weight of the roll that resists its vertical movement, serves to break the bond between adjacent hook and loop sides of the strap that is rolled upon itself. Following separation pin 22, the tape 20 passes through a retarding path 24 defined between a flat spring 26 and a land surface 30 defined by the housing structure of the dispenser.

In the embodiment shown, spring 26 is of blue spring steel, flat in orientation. It extends from mount 29 as a cantilever and has an end portion 28 that extends substantially parallel to land 30, against which it is spring biased, such that, in the absence of tape 20, the spring portion 28 engages the land 30. Two screws 35 are perpendicular to the plane of the spring, and go up vertically. Parallel to the right hand side beyond the screw holes 35 is the end of the pocket 27. The depth of the pocket 27 provides enough depth to recess the screw head.

In the presence of the tape, respective faces of the fastener tape are engaged, the spring serving to maintain the emerging part of the strap raised to be grasped and to frictionally retard the tape as the tape is pulled from the dispenser. The moderate predetermined drag provided by the retarding path ensures that the product does not pull out too freely during normal application of withdrawing tension, and it provides resistive tension for enabling the initial phase of the singulating action now to be described.

Following the retarding path, the fastener tape extends freely through access region 32 at which it can be initially grasped by the user. The tape path then extends through guide channel 34 which is open at the top. Guide channel 34 is defined by two side guide members 36, 37, disposed to be engaged by the edges of the tape, and a downwardly curved lower surface 38 against which the user draws the tape, as the user pulls downwardly and rightward against the resistance provided by the spring which deflects. In this embodiment, one of the guide members 37 is a portion of the structure of the removable cover 16, and the other side guide 36 is integral with the main housing of the dispenser.

Each guide 36, 37 is sufficiently rigid to engage and guide the edges of the strip material which it is adapted to dispense. The two guides 36, 37 thus provide a centering action, to guide the tape so that it registers with a detent device 40 located in the guide channel 34.

In the present embodiment, the detent device 40 is a stationary claw, shaped much like a cat's claw, directed upwardly and hooked backwardly to oppose motion of the strip. The claw tapers slightly to a dull point, which is disposed to be slidably engaged by the underside of the tape as the user, with downward and forward force, draws the tape through the guide channel, against curved surface 38. The tape thus slides over the apex of claw 40. In this embodiment the claw 40 is centered in the middle of the guide channel between the two side plates 36, 37. The shape of the claw is shown in FIGS. 1B and 1C.

Figure 1A:
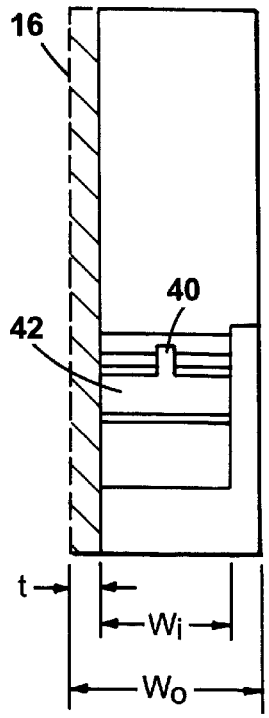
FIG. 1A is a front view of the dispenser.
Figure 1C:
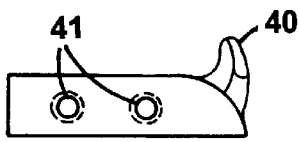
FIG. 1C is a side view of the claw included in the dispenser in FIG. 1.
Figure 1D:
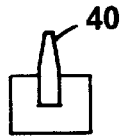
FIG. 1D is a frontal view of the claw shown in FIG. 1C.
Figure 1B:
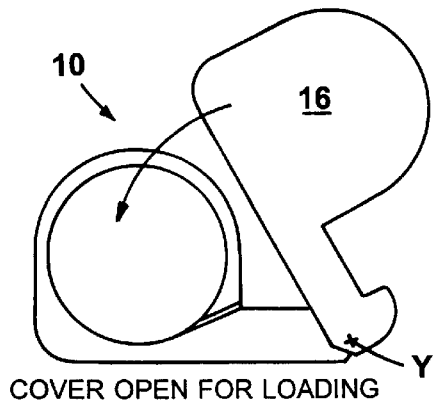
FIG. 1B is a side view of the dispenser similar to FIG. 1, with the cover shown in its position for loading.
Figure 3:
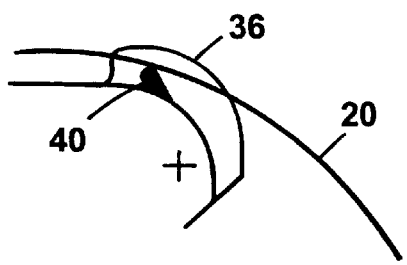
FIG. 3 illustrates a fastener strap being pulled from the dispenser.

In FIG. 1A, a side view of the dispenser (cover 16 shown by dashed lines), the elevation of claw 40 from the body 42 of the claw holder is illustrated. In this embodiment claw 40 is formed integrally with the structural body 42, the claw profile having been provided by a separate piece that is inserted into the body 42. The claw body has mounting holes 41 for attachment.

(In production versions formed by injection molding, the claw is of impact structural resin, e.g. acrylonitrile butadiene styrene (ABS)/or high impact polystyrene, integrally formed with the dispenser housing.)

The detent 40 between the two side plates, rounded as to accommodate sliding movement of the tape, stands up and indents the tape as the tape, being drawn by the user from the dispenser, is pulled in rightward, downward motion (FIG. 3), overcoming drag applied to the tape by spring 26.

Figure 4:
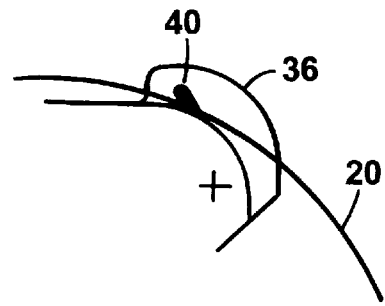
FIG. 4, similar to FIG. 3, shows the strap material being engaged by a detent immediately before separation of the leading strap from the roll.

When a formation provided in the strip material at the juncture of the leading strip units and the following units reaches the claw, the claw penetrates the substance of the tape, as shown in FIG. 4 and resists further motion of the following strip unit to the degree that the line of weakness ruptures under user's tension and the leading strip unit is separated from the supply.

Figure 6:
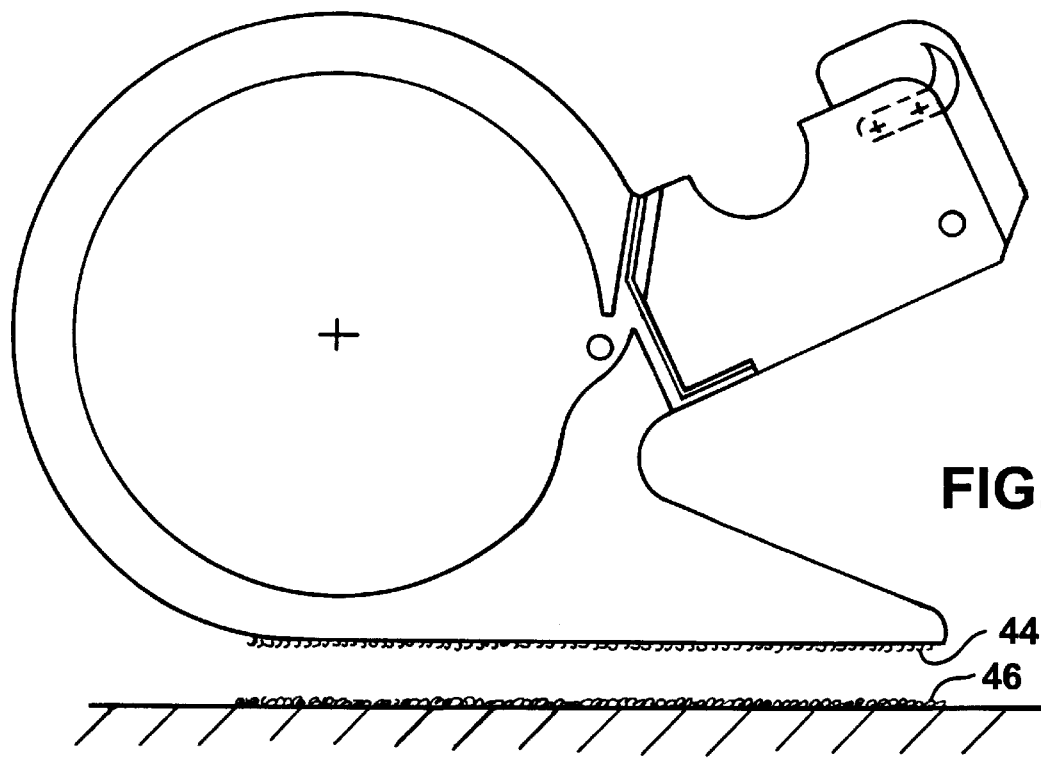
Figure 6A:
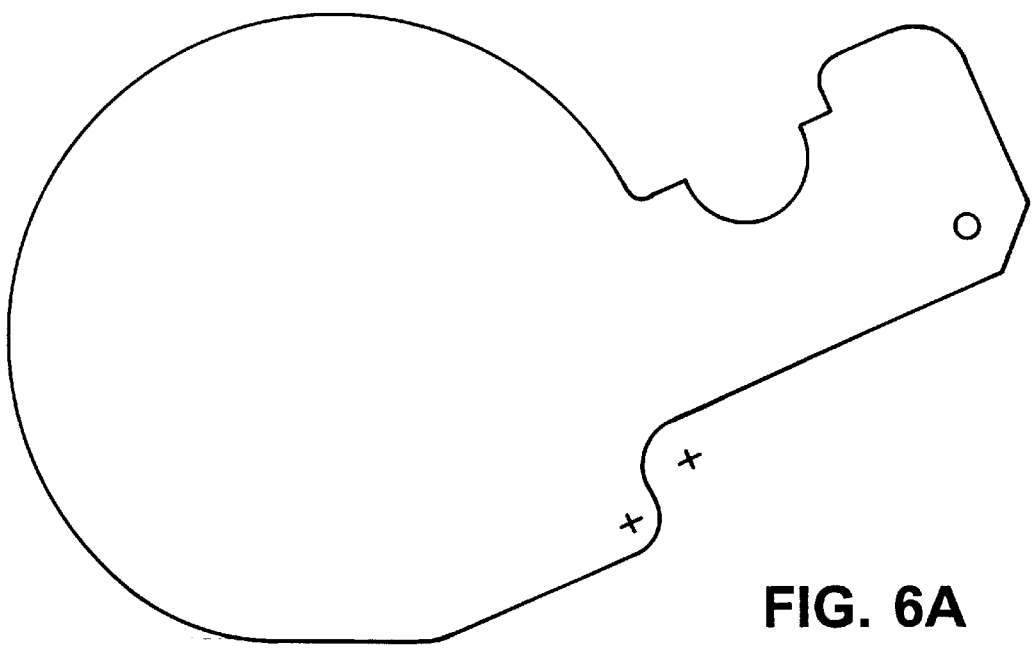
FIG. 6A is a side view of the cover used with the dispenser of FIG. 6.
Figure 6B:
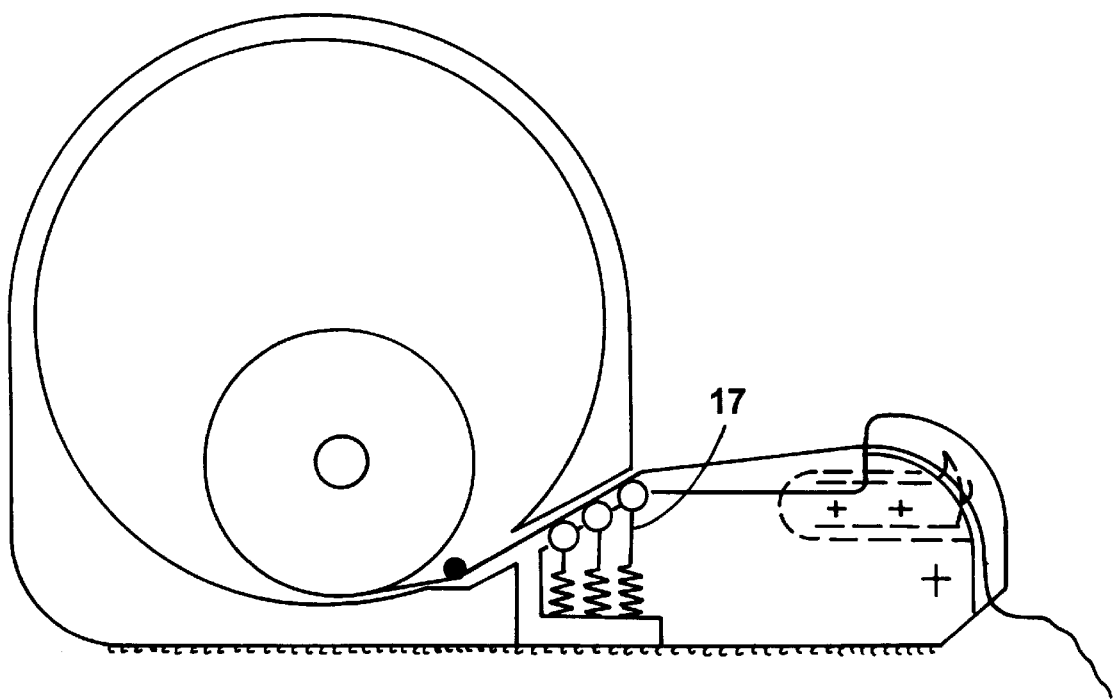
FIG. 6B is a side view of a dispenser, having three spring rollers to apply pressure to the strap material to be dispensed.

As illustrated in FIG. 6B, in order to work with the fastener having tape adhesive on its backside, three spring rollers 17 replace the flat spring 26 and engage the adhesive. The rollers are adjustably spring loaded; drag is provided to the strap by the contact of the non-adhesive side of the product against the body of the dispenser.

FIGS. 6 and 6A illustrate an alternative configuration of the dispenser, where the dispensing section is angled to enable the user to pull strip material straight out of the dispenser at an upwardly inclined angle, when the dispenser is resting on a flat surface.

Figure 6C:
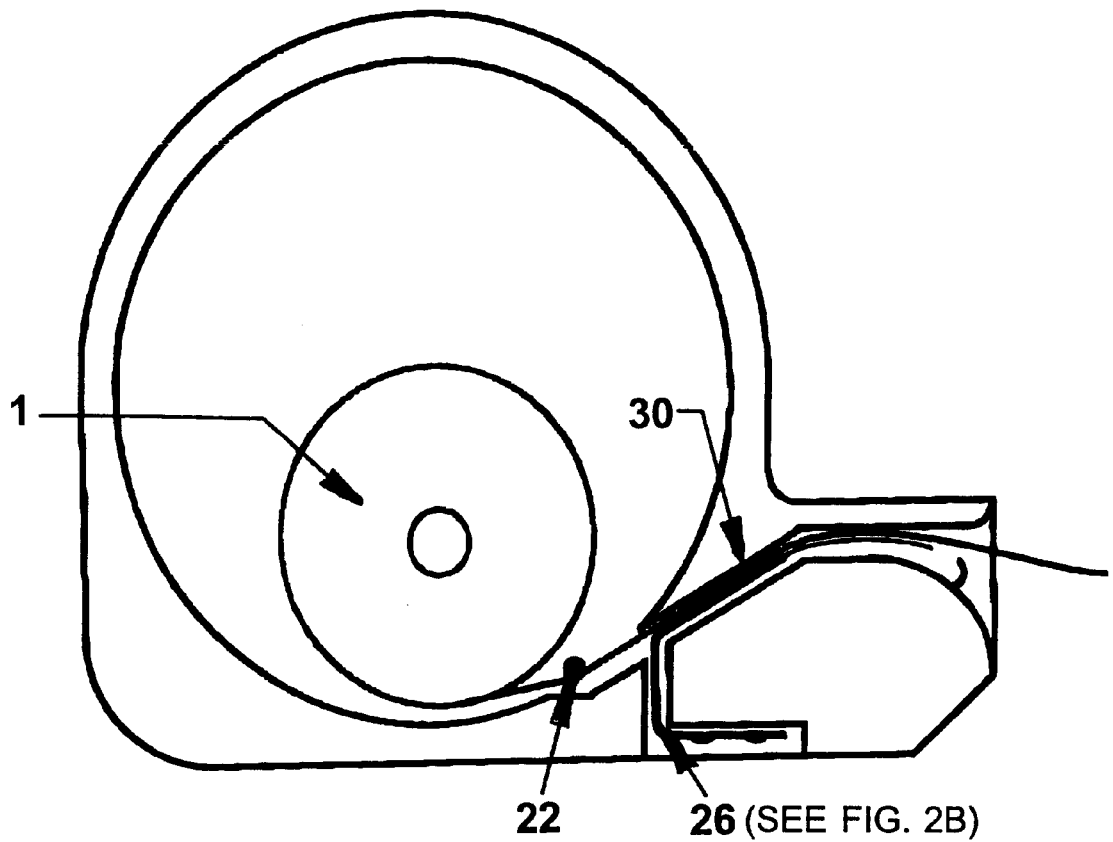
FIG. 6C is a view similar to FIG. 1 of a dispenser construction, having the tensioning system illustrated in FIG. 2B.

In another embodiment, shown in FIG. 2A, spring 26 has a curved end. This shape enables the user to smoothly pull a strap out of the dispenser without scratching the strap's surface, and without damaging printing which might be placed on the strap. Alternatively, the end of the spring 26 can have a thinned cross section, as illustrated in FIG. 6C and in detail in FIG. 2B. The flexibility provided by the thinned section enables the strap to be pulled out of the dispenser without relieving the drag provided by rearward portions of the spring. When pulling tension is discontinued, the end of the spring restores toward its straight configuration, lifting the fastener into position to be grasped.

Figure 7:
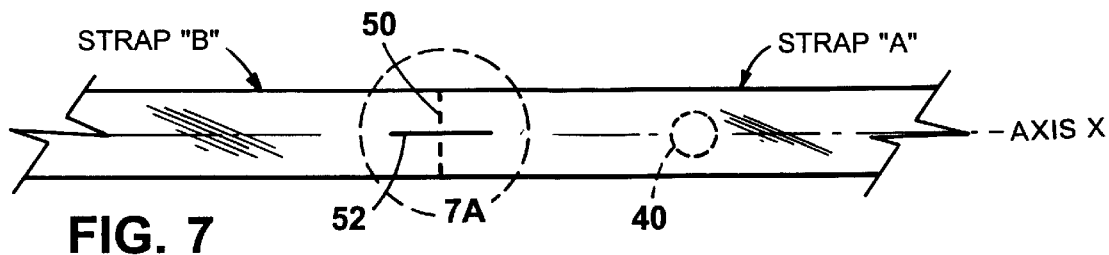
FIG. 7 is a top view of two straps defined by a line of perforations and having a longitudinal slit in adjacent ends.

Referring to FIG. 7, leading and trailing straps A and B are shown with a line of perforations 50 between them, extending from edge to edge of the strap, perpendicular to the longitudinal center axis X of the strap.

Figure 7A:
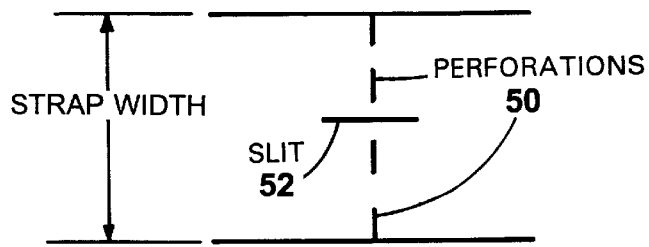
FIG. 7A is a magnified view of the perforation and slit of FIG. 7.

The magnified view of FIG. 7A shows a blown-up version of the slit 52 and perforations 50. In this embodiment, the slit is approximately ½ inch long, ¼ inch in each of straps A and B, and is shown centered widthwise and extends perpendicular to the line of perforations 50. The slit and perforations are readily formed with a rotary die system or a stamping system or a laser cutting system through which the strap material is passed before it is formed in rolls.

A longitudinal slit 52 cut through the thickness of the strap is formed in the adjacent end regions of straps A and B at their juncture, this slit being aligned with longitudinal strap axis X.

Figure 5:
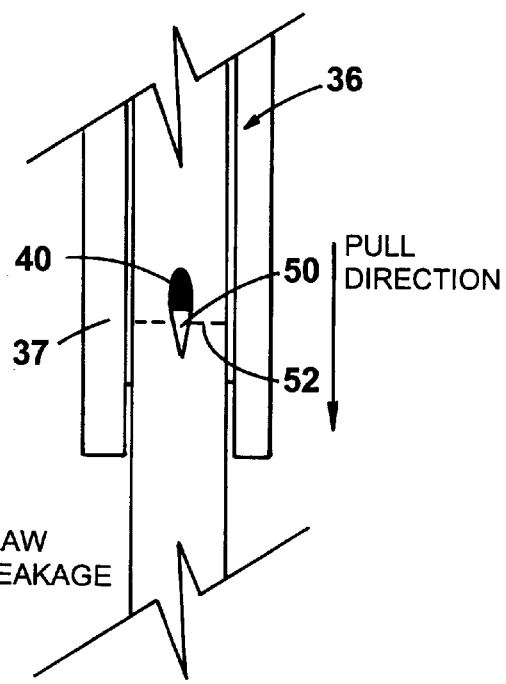
FIG. 5 is a top view of the strap of FIG. 4 being engaged by the detent.

As Strap A is pulled from the roll 14, it moves across the detent 40, shown in dotted lines. Referring also to FIG. 5, the detent claw is in axial alignment with the center axis X of the strap and slit 52.

As slit 52 approaches the detent 40, the claw feature 40 enters the leading part of slit 50 defined in lead strip A. Hook 40 penetrates the thickness of the tape, and, under downward and rightward tension applied by the user to the lead unit, the tape is free to move downwardly against the curved surface 38. The strap continues to move from the dispenser until the end of the slit 52, defined by the trailing strap unit B, reaches the claw. The claw resists further movement of the strap and as the lead strap continues to be pulled by the user, the materials breaks at the line of perforations 50, freeing the lead strap unit A from the supply. The spring 26, due to its strength and orientation, raises the portion of the trailing strap unit emerging into region 32, making the unit B available to be grasped. The action of spring 26 pulls strap B from the claw 40.

Figure 8:
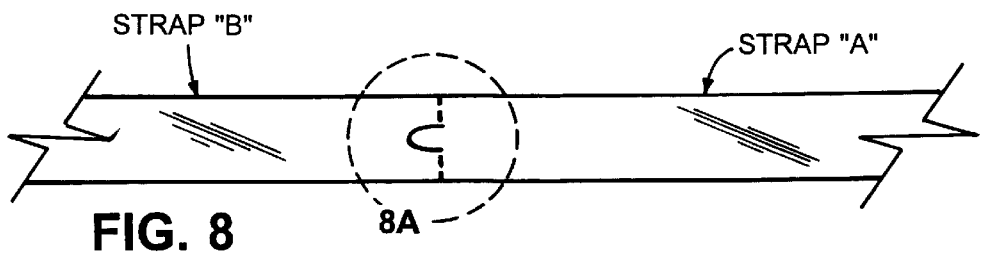
FIG. 8 is a top view of two adjacent straps, having another type of formation at their juncture.
Figure 8A:
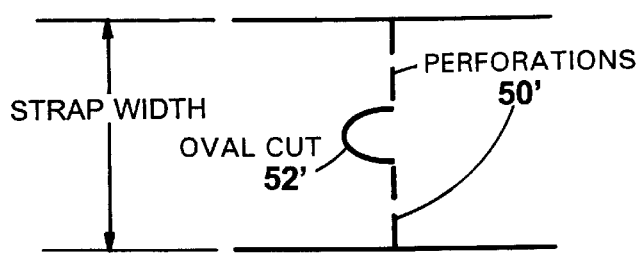
FIG. 8A is a magnified view of the features illustrated in FIG. 8.
Figure 8B:
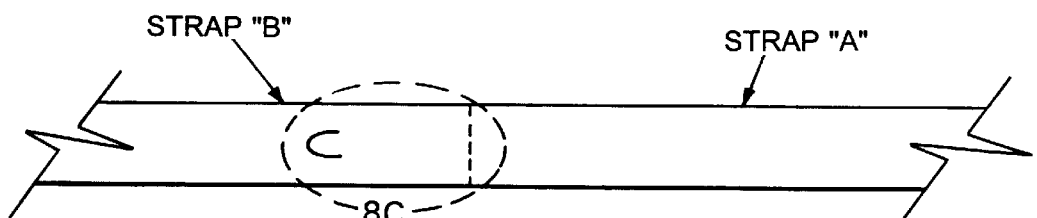
FIG. 8B is a top view of two adjacent straps, having another type of formation at their juncture, with the oval cut formation somewhat displaced from the juncture.
Figure 8C:
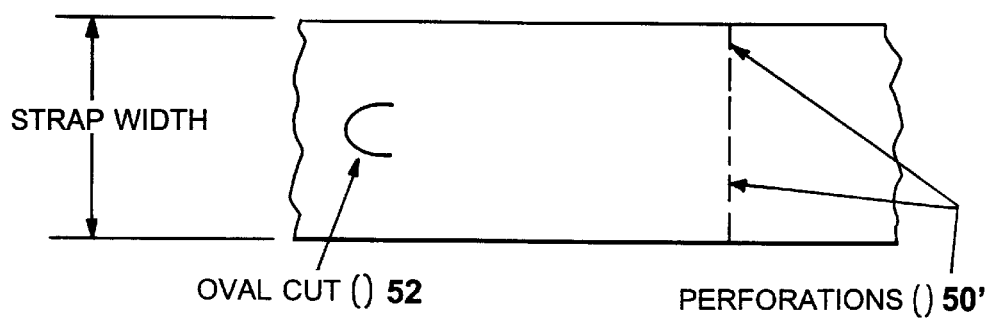
FIG. 8C is a magnified view of the features illustrated in FIG. 8B.

FIG. 8B illustrates still another tape construction which has a line of perforations 50' similar to those in FIGS. 7 and 8. However, the oval formation 52', which in FIG. 8 is placed directly at the line of perforations, is moved some distance into the strap. This arrangement results in the trailing strap protruding some distance from the dispenser after the leading strap has been severed, making it even more convenient for the user to grasp the next strap.

The length and spring force of the spring 26 is selected to perform its dual function of applying drag as the strap is withdrawn, and of raising the strap material when the preceeding strap breaks at the perforations, to position the next strap in a convenient manner for the user to grasp.

Another tape construction, shown in FIG. 8, has a line at perforations 50' similar to those of FIG. 7. However instead of a straight slit, there is an oval cut formation 52'. The oval cut formation provides a benefit in that it helps avoid longitudinal rips in those tape constructions which are susceptible to longitudinal ripping failure. The oval formation 52' serves to spread the load applied by claw 40 to the trailing strap, and thus lessen the stress applied to the trailing strap. The oval formation is advantageous, for instance where the base layer of fastener hook tape being dispensed is thin and not sufficiently reinforced to prevent propagation of a failure line. A larger oval formation helps keep the tape from catching on the claw.

Figure 9:
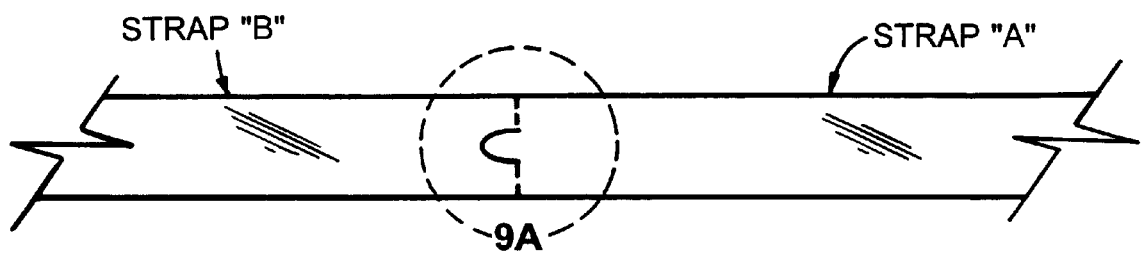
FIG. 9 is a top view of two adjacent straps, having another type of formation at their juncture.
Figure 9A:
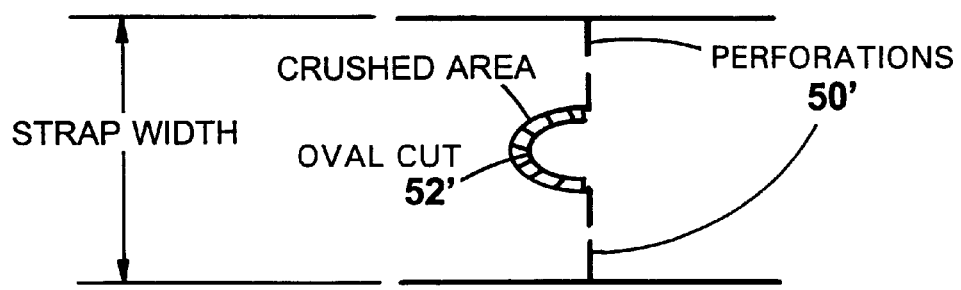
FIG. 9A is a magnified view of the features illustrated in FIG. 9.

The strap of FIGS. 9 and 9A shows straps, perforations, and cut through similar to those of FIG. 8, with an additional crushed area 54 around the oval, formed by a die that deforms by compression. The crushed or depressed area enables the user to see the beginning and end of the strap when it is in non-broken form, as it approaches the detent.

For forming the crushed area in a hook or loop fastener tape, a land is provided in the die or stamping tool of about $\frac{1}{16}$" width; its pressure crushes all the features of the hook or the loop and is shaped to cut through on an edge of the crushed region to form the oval cut.

The braking action of the spring which enables tension to be applied on the strip and which prevents overfeed, enables the mechanism to be used in one-handed operation. For this purpose, the device is attached to a table, or is otherwise secured to resist the tension applied by the user to the dispenser. (In the preferred embodiment shown, hooks 44 are integrally molded in the base of the dispenser, and the dispenser is packaged with a strip of adhesively backed loop material 46. The loop material is adhered to a bench or other surface, and the dispenser is releasably secured to the loop materials, by resting upon it, with its hooks engaged in the loops.)

The side guides 36, 37 provide alignment between the claw feature 40 and the slit feature 52, 52' that have been cut into the straps. The bigger the hole that is slit or punched through the strap, the lower are the alignment requirements. However, a degree of strength is required so that the straps stay connected until it is necessary that they be broken. As one increases the size of the feature which the claw 40 engages to hold the strap back, one decreases the available strap width that remains for strength purposes.

In another alternative, an angled slit is provided that extends along the length of e.g. the center half of the tape, so there is a ¼" on each side, but angled. In this embodiment, the claw feature 40 is able to find it, regardless of the alignment. However, as the height of the claw feature of the detent 40 increases, the stability of the narrow web riding on the top of it without guides becomes less sure. The detent 40 has to be sufficiently high to find the slit; in the case of a diagonal cut, it must extend through sufficiently that the strap cannot ride off it so that it is captured.

The slit or other formation in the strap does not have to be symmetrically disposed or centered so long as the dispenser enables the strap to be guided into engagement with the hook or hooks or other detent.

In another embodiment, the dispenser is manufactured by injection molding techniques as two halves constructed to be releasably joined (or permanently joined with a roll of tape inside with which the dispenser is provided as a disposable unit). One injection molded half, for instance, is constructed to slide over the other half to capture the supply roll.

In a preferred example of such case, the separation pin 22, the land 30, and the claw feature 40 are all injection molded as integral parts of the plastic housing structure.

The spring 26 may be separately formed and inserted into the assembled structure, or it may be injection molded to become integrated with one of the injection molded parts. The spring may for instance be blue spring steel or an impact-resistance plastic.

Referring to FIGS. 10 and 10A, straps A and B are comprised of rows of molded hooks 80, alternate rows facing in opposite directions. The hooks molded integrally with base layer 82 and the straps have in situ bonded to their lower surface non-woven loop material 84 that forms loops of suitable dimensions to be releasably engaged with hook 80. In a preferred form for use in low cost applications, the non-woven fabric is a needled and stretched loop material described further below.

The concepts that have been presented have wide application where singulation of a fastener strip product is required. Singulation with one hand is enabled.

In one preferred embodiment, the dispenser is constructed to be portable, e.g. hand-held. It is held in one hand and brought to the object that is to be wrapped. The user either pulls the strap or pulls the dispenser so that the strap unrolls and is wrapped about the object.

Using the hook and loop product from the dispenser offers advantages of speed: once it is wrapped around the product, it sticks to itself and is secure. Identification information can be printed on the hook or loop side of the product.

Another advantageous feature is that the hook and the loop product can be reused. For instance, if wires, fiber optics or other items should need to be added or removed from the bundle, the strap may be undone, the item added or removed, and the strap re-engaged upon itself. The hook and loop product is not significantly affected by moisture, cold, oil, grease and other contaminants and maintains good appearance and its action is still secure after multiple openings and closings. Furthermore, by using the dispenser and applying the tape with the loop side in, a cushioning effect is obtained upon the objects being bundled, preventing abrasion or bruising.

An application is in bundling wires, cables, and hydraulic and pneumatic lines. In the case of telecommunication fiber cables where two-sided hook and loop products are commonly used, the dispenser, for instance, enables significant reduction of the time necessary to singulate straps.

The dispenser may be employed by packers for household moving, to put tape on boxes, for instance with pressure-sensitive materials. In one such case a hook tape is provided that has pressure-sensitive adhesive on its back side and perforated as illustrated here, and another tape which is loop that also has pressure-sensitive adhesive, and is perforated in the same way. Pre-formed pieces of those two fastener components are rolled upon themselves and the rolls mounted in a dual dispenser, side by each, to enable application of each to bags, boxes, etc. to provide a releasable closure system that may be opened and closed repeatedly.

This dispenser may be modified in many ways while still employing important features. In one case a spring lever is advantageously added to the side of the dispenser, associated with an advancing mechanism that is activated by pushing the lever down, to advance the strap. At the time one releases the lever, one would cut a strap of desired length much like the action of traditional paper tape dispensers. This permits use of the dispenser also with strips that do not have the perforated lines of weakness and other features.

The dispenser can also be automated in which the pulling tension is applied by e.g. a robot or another device that grasps the free end and draws it from the dispenser as in the manner described.

The dispenser can be used with a variety of fastener strip material, where the strap material has arrays of fastener elements on both of its sides which are capable of being releasable fastened together. Examples of such elements are hooks and loops. The hooks can be molded integrally with a base layer and the material providing loops including fibers that serve the function provided by textile loops can be joined by the material of the base layer. The loop side of the material can advantageously be a low-cost non-woven web of entangled fibers of substantial tenacity with a basis weight of between 1.8 to 2.5 ounces per square yard.

The loop material can advantageously comprise a batt of loose, staple fibers that have been entangled and form a non-woven fabric of fibers joined at entanglements, with loops of some of the fibers extending from at least one side of the fabric. Advantageously, needling of the batt is employed to form the entanglements. In some embodiments, the non-woven fabric is bonded in a stretched state in which tightened entanglements form knots. The non-woven fabric can also be bonded in a stretched state by resin integral with the material that forms the hook-form fastening elements. Non-woven material for forming such fastener elements and its method of manufacture is more fully described in our co-pending application U.S. application Ser. No. 08/922, 292, filed Sep. 3, 1997, entitled FASTENER LOOP MATERIAL, ITS MANUFACTURE, AND PRODUCTS INCORPORATING THE MATERIAL, which is hereby incorporated by reference.

As has previously been indicated with reference to FIGS. 7–10, fastener material suitable for use with the dispenser can be prepared in the form of an extended length of strip material defined as a series of detachable straps. For use with the dispenser detent, the material has formations including weakened parting lines at spaced intervals along its length and at least one formation constructed and arranged to be engaged by the detent to detain the remaining length of fastener material while the leading strip is detached by rupture at the parting line by tension applied to the parting line.

This material is provided with sufficient lateral stiffness to enable it to be guided by edge guides, to register the detent with the formation at the leading end of each strip. Furthermore, it is advantageous that the material have sufficient thickness and stiffness to spring from a bent configuration as it is pulled across the detent to a more planar shape when the leading strip is broken from the remaining material so that the freed end of the remaining material lifts from the detent in a position where it can be readily grasped by a user for dispensing the next successive strip as the new leading strip.

Adhesive-Backed Hook or Loop With Release Layer

Various types of fastener materials having pressure sensitive adhesive on the side opposite the fastening elements are provided with a release layer, and the lines of perforations are made through both the fastener material and the release layer, thereby enabling simultaneous separation of all layers by the dispenser.

Printing on Straps

For certain applications, it is useful to have text printed on the separable straps, for instance to provide label information such as product codes, bar codes, identification of bundled elements for telecommunication, instructions or warnings. Such information may be preprinted on the hook or loop portion of the straps.

Manufacturing Methods

Advantageously following the techniques disclosed in U.S. patent application "Fastener Loop Material, Its Manufacture and Products Incorporating the Material", referenced above, a lightweight, non-woven loop material is produced. It comprises a non-woven web of entangled fibers of substantial tenacity, the fibers forming a sheet-form body and hook-engageable free-standing loops extending from the web body. The web is stretched before bonding to produce spaced apart loop clusters extending from a very thin web of taut fibers, and binder can be added to stabilize the product in its stretched condition. The backside of the loop product is then combined with the back side of a layer that carries hook fasteners; this combining step can be effective to bind the knots to hold the fabric in its stretched condition, to serve the function of the binder just mentioned.

This hook-engageable material is then used for forming a composite product having a large multiplicity of hook-form fastener projections extending from the opposite surface. For this purpose a cooled, rotating mold roller is provided having inwardly extending, fixed, projection-forming cavities defined in its periphery, to the exterior of the forming roller, molten plastic material is applied for filling the cavities and forming a base in the manner that incorporates the hook engageable material on the side of the base opposite from the side in which the projections are formed, the fastener material is withdrawn from the forming roller in a step that includes withdrawing the projections from the cavities, and either in line or as a separate batch process, parting lines are formed at spaced intervals extending transversely of the strip material.

Advantageously the non-woven material is laminated in situ with the hook material using a layer of resin that forms the base of the hook material to bond directly to the non-woven, as generally taught by Kennedy et al. in U.S. Pat. No. 5,260,015.

Figure 11:
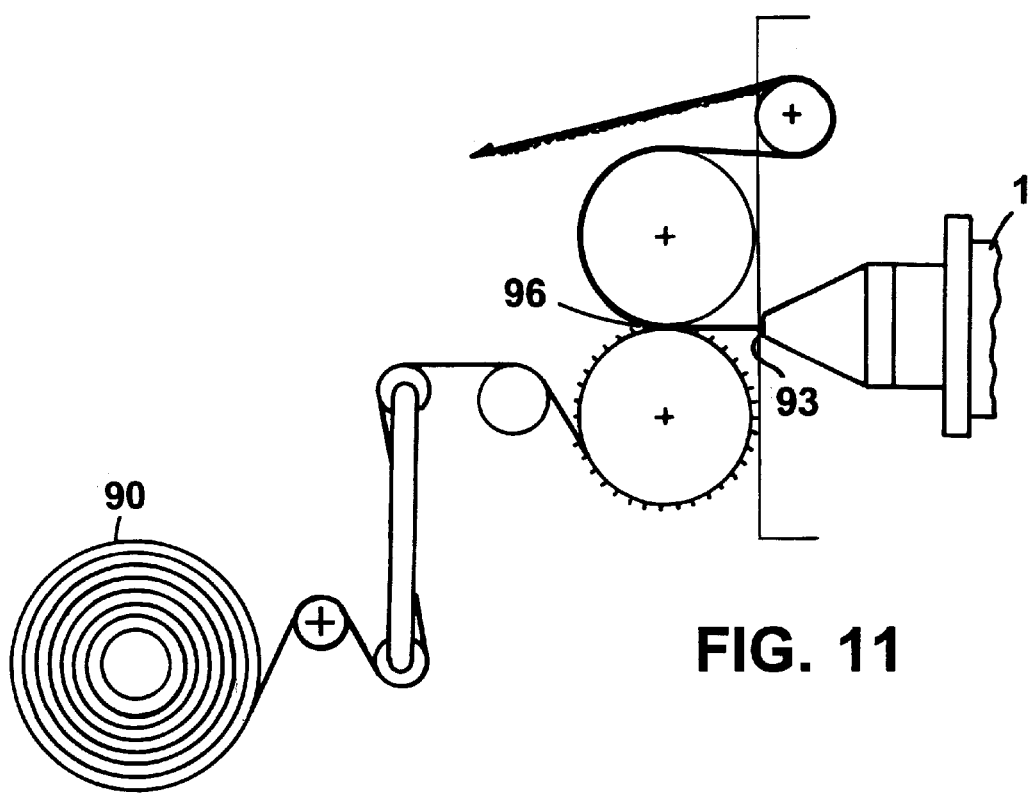

In the case of using the specific example of FIG. 2 of the Kennedy et al. patent (FIG. 11 of this application) a preformed sheet material 90 is forced into the nip 96 at the same time as molten plastic 93 is forced into the nip 96 to create strip fastener tape, the sheet material bonding intimately with the fastener to become an integral part of the structure of the strip fastener.

Figure 12:
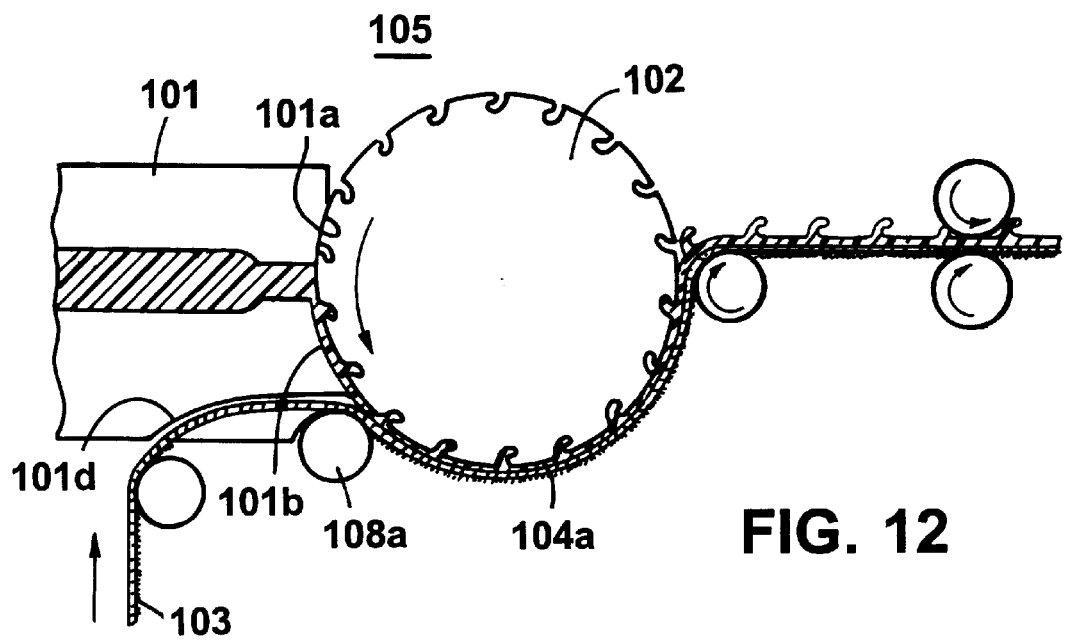
FIG. 12 is a variation from FIG. 11, based on the same general principles.

Another case which utilizes the same general concept, is the specific system illustrated in U.S. Pat. No. 5,441,687, Murasaki et al. At the front end surface of the upper half of the extrusion nozzle 1 shown in FIG. 1 of that patent (FIG. 12 of this application), there is an upper arced surface 101a, the curve of which mirrors that of the die wheel 102, while at the front end surface of the lower half of the nozzle 101, there is a further lower arced surface 101b, the curve of which also mirrors that of the die wheel.

A guide channel 101d through which the non-woven material is introduced is formed in the lower half of the extrusion nozzle 101. A rear pressure roller 108a applies pressure between the sheet of molten resin extruded from the extrusion nozzle, to join the non-woven material 103 to be attached to the resin.

Thus in operation the molten resin extruded from the extrusion nozzle 101 is forced into the gap between the die wheel 102 and the lower arced surface 101b, and fills up the hook molding cavities 105 along with a base layer 104a of fixed thickness and width. At the same time as this molding process is taking place, the backing material 103 is guided up through the backing material guide channel 101d in the extrusion nozzle 101 and is pressed against the surface of the molten base layer 104a by the rear pressure roller 108a to firmly join them together, so that the bases of the loops in the backing material are firmly held by the resin so that the loops will hold their shape well and will be very durable.

Various preferred embodiments of the invention have been presented. However, the illustrations are not exhaustive; it should be readily apparent to one skilled in the art that other configurations of the dispenser and the strap material are possible, including use of alternative strap material configurations and arrangements within the dispenser.

What is claimed is:

1. A dispenser for a supply of continuous fastener strip material, the material having formations that include parting lines spaced at points along the length to define successive units of predetermined length, and engagement formations adapted to be engaged by the dispenser for resisting movement of the strip material, the parting lines enabling a leading unit to part from the remaining material when the material at the respective parting line is subjected to parting tension, the material also having an array of loop-engageable projections extending from a broad surface thereof, the dispenser comprising a receptacle to hold the supply of strip material, a retarder constructed and arranged to provide drag against the motion of the material as a leading unit is removed from the dispenser in response to pull by a user, and a device positioned to be engaged by the strip material as the leading unit is pulled from the dispenser, said device comprising at least one detent constructed to engage a corresponding engagement formation of a remaining unit following the leading unit to resist movement of the remaining unit so the leading unit parts from the remaining material at the respective parting line.

2. The dispenser of claim 1 in which said device is located downstream of said retarder.

3. The dispenser of claim 1 in which said receptacle is constructed and arranged to hold a supply of fastener strip material having parting lines defining strip-form fastener units.

4. The dispenser of claim 3 in combination with a supply of fastener strip material having fastener elements on at least one of its sides.

5. The combination of claim 4, in which the fastener elements comprise hooks for hook and loop fastening.

6. The combination of claim 4 in which the fastener elements comprise fibers or loops adapted to be engaged by hooks or hook like elements for hook and loop fastening.

7. The combination of claim 4 in which the fasteners are constructed for self-engaging fastening.

8. The combination of claim 4 in which the fastener strip material is two-sided, having hooks on one side and fibers or loops engageable by the hooks on the other side.

9. The combination of claim 4 in which the fastener strip material is two sided, having hooks or hook-engageable loops or fibers on one side and pressure-sensitive adhesive on the other side.

10. The combination of claim 9 in which a release layer lies over the pressure sensitive-adhesive and the parting line extends into the release layer.

11. The dispenser of claim 1 in which the detent comprises at least one stationary claw over which the strip material slides as the leading unit is pulled from the dispenser until a formation of the second unit of strip material that is engageable by the claw is engaged by the claw.

12. The dispenser of claim 1 in which said retarder includes a resilient member that bears against the strip material as the leading strip unit is withdrawn.

13. The dispenser of claim 2 in which said retarder includes a leaf spring.

14. The dispenser of claim 13 in which the downstream end of said leaf spring is positioned and arranged to be resiliently deflected in response to pull upon the leading strip-form unit.

15. The dispenser of claim 14, wherein the downstream end of said leaf spring is curved away from a path of the strip material.

16. The dispenser of claim 2 in which said retarder includes a resilient member constructed and arranged to position the next-following unit for grasping upon breaking of the leading unit from the remaining material.

17. The dispenser of claim 16 in which said resilient member is constructed and arranged to raise a portion of the strip unit immediately following the leading unit upon breaking of the leading unit from the remaining material.

18. The dispenser of claim 17 in which said resilient member comprises an elongated spring member exposed for face-to-face engagement with the under-surface of the strip material, positioned to raise the end of the next-following unit when the leading unit is broken away.

19. The dispenser of claim 18 wherein the downstream end of said spring member is arranged to be resiliently deflected downwardly by withdrawing tension applied to the leading strip unit, and, upon relief of the tension as a result of breaking of the leading unit from the remaining strip material, said spring is constructed and arranged to move upwardly in restoring motion to carry with it the strip material that extends beyond the spring into position to be grasped.

20. The dispenser of claim 18, wherein the leaf spring member has a main portion at said retarder and wherein a downstream end portion of said leaf spring beyond the retarder is thinner than the thickness of the main portion of said leaf spring, the downstream end portion arranged to be resiliently deflected during removal of a leading strip and to elastically recover upon parting action of the leading unit, carrying with it the corresponding portion of the successive unit.

21. The dispenser of claim 1 wherein said retarder includes a spring-loaded roller.

22. The dispenser of claim 1 in which hooks are integrally molded on a portion of its exterior, enabling said dispenser to be releasably mounted on loop material secured to a support.

23. The dispenser of claim 1 in combination with a supply of strip material, units of the material having slits engageable by the detent, each slit ending at a stop surface that enables said detent to stop movement of the second unit.

24. The dispenser of claim 1 in combination with a supply of strip material, units of the material having formations exposing detainable edge portion of the unit for engagement by said detent.

25. The dispenser of claim 24 in which the detainable portions are located at the leading ends of their respective units.

26. The dispenser of claim 24 in which the detainable edge portions are located in the main body of the respective units.

27. The dispenser of claim 1 in combination with fastener material of strip form which has sufficient stiffness and roll set (curl memory) to spring from a bent configuration as it is pulled across the detent to a straighter or reversely curved shape when the leading unit is broken from the next succeeding unit so that a portion of the next unit lifts from the detent in position to be grasped by a user for dispensing.

28. The dispenser of claim 1, constructed to hold a supply of strip material in roll form.

29. The dispenser of claim 1, constructed to hold a supply of strip material folded upon itself in a Z-fold.

30. The dispenser of claim 1, constructed and arranged to enable withdrawing a strip unit by one hand of a user.

31. The dispenser of claim 1 comprising a base suitable for resting upon a flat surface.

32. The dispenser of claim 1, constructed and arranged to be portable or hand-held.

33. The dispenser of claim 1 wherein the dispenser has hooks integrally molded on a portion of its exterior enabling the dispenser to be releasably mounting on loop material secured to a support.

34. The dispenser of claim 1 having a base suitable for resting upon a surface having a given orientation, and a dispensing section angled away from the given orientation so that a strip unit can be withdrawn at that angle.

35. The dispenser of claim 34 having a base constructed to be mounted on a horizontal surface and the dispenser section is upwardly angled.

36. The dispenser of claim 1 comprising edge guides for engagement by edges of strip material being withdrawn from the dispenser to guide the material to be engaged by said detent in the formation provided in the material.

37. The dispenser of claim 1 in combination with a supply of fastener strip material having substantial lateral stiffness, the dispenser including edge guides in the vicinity of said detent to guide the fastener strip to ensure the detent engages the respective formation in said strip material.

38. The dispenser of claim 1 combined with a supply of fastener strip material to be dispensed, the strip material carrying arrays of fastener elements on its first and second sides, the respective fastener elements being of cooperative form capable of being releasably fastened together.

39. The combination of claim 38 in which the fastener elements on the first side comprise loops or fibers of form capable of being releasably engaged by fastener elements on the second side.

40. The combination of claim 39, wherein the fastener elements on the second side of the material are hooks molded integrally with a base layer, the loops or fibers being bonded to the base layer of the molded hooks by the material of the base layer.

41. An extended length of fastener material forming a series of detachable strip units suitable for use with a dispenser having a detent, said fastener material having
a strip-form base defining therein formations that include weakened parting lines at spaced intervals along its length to define the strip units therebetween and at least one engagement formation within each strip unit, the engagement formation constructed and arranged to be engaged by said detent to detain the respective unit while a preceding unit is detached by rupture at the parting line by tension applied to the parting line; and
an array of loop-engageable projections extending from a broad side of the base.

42. The fastener material of claim 41 in which the strip material has sufficient lateral stiffness to enable it to be guided by edge guides to register said detent with said formation of each strip unit.

43. The fastener material of claim 41 in which the material has sufficient resiliency to spring from a bent configuration as it is pulled across a detent to a straighter shape when the leading unit is broken away from the remaining material to assist the succeeding unit to lift from said detent in position to be grasped by a user for dispensing the next successive strip unit.

44. The fastener material of claim 41 in which the loop-engageable projections comprise hooks integrally molded with resin of the base.

45. The fastener material of claim 41 further comprising, on a side of the base opposite the projections, loops or fibers of form capable of being releasably engaged by the projections.

46. The fastener material of claim 41 in which the engagement formations expose detainable edge portions of each strip unit for engagement.

47. The fastener material of claim 46 in which the detainable portions are located at the leading ends of the strip units.

48. The fastener material of claim 46 in which the detainable edge portions are each located within the main body of a respective strip unit.

49. The fastener material of claim 41 in which the engagement formations comprise engageable slits.

50. The fastener material of claim 41 further comprising pressure-sensitive adhesive on a side of the base opposite the projections.

51. The fastener material of claim 50 further comprising a release layer over the pressure sensitive-adhesive, the parting lines extending into the release layer.

* * * * *

UNITED STATES PATENT AND TRADEMARK OFFICE
CERTIFICATE OF CORRECTION

PATENT NO.     : 6,235,369 B1
DATED          : May 22, 2001
INVENTOR(S)    : William H. Shepard It is certified that error appears in the above-identified patent and that said Letters Patent is hereby corrected as shown below:

<u>Title page,</u>
Item [75] Inventor, please delete Paul R. Erickson as an inventor.

Item [56] References Cited,
U.S. Patent No. 4,267,949, "Hembren" should be -- Hemgren --.

Signed and Sealed this

Fifth Day of March, 2002

*Attest:*

*Attesting Officer*

JAMES E. ROGAN
*Director of the United States Patent and Trademark Office*